United States Patent [19]

Malley

[11] Patent Number: 4,545,986

[45] Date of Patent: Oct. 8, 1985

[54] TIMOTHY GRASS ANTIGEN SPECIFIC ANTI-IDIOTYPIC ANTIBODIES

[75] Inventor: Arthur Malley, Portland, Oreg.

[73] Assignee: Research Corporation, New York, N.Y.

[21] Appl. No.: 390,923

[22] Filed: Jun. 22, 1982

[51] Int. Cl.$^4$ .................. A61K 39/395; A61K 39/36; A61K 37/02; C07G 7/00; C12P 2/00; C12N 5/00; C12N 5/02

[52] U.S. Cl. ........................................ 424/85; 424/88; 424/91; 514/2; 260/112 R; 260/112 B; 435/68; 435/240; 435/241

[58] Field of Search ............... 424/88, 85, 91; 435/68, 435/240, 241; 260/112 B, 112 R

[56] References Cited

PUBLICATIONS

Malley, A., and Deppe, L., Int. Arch. Allergy Appl. Immun., vol. 63, pp. 113-120, 1980.
Malley et al., Immunology, vol. 45, pp. 217-225, 1982.
Malley et al., "Induction and Characterization of Suppressor T Cells and Soluble Factors with Modified Timothy Grass Pollen AgB", International Archives of Allergy and Applied Immunology, vol. 65, pp. 129-151 (1981).
Blaser et al., "Suppression of Anti-Hapten IgE and IgG Antibody Responses by Isologous Anti-Idiotypic Antibodies Against Purified Anti-Carrier (Ovalbumin) Antibodies in BALB/c Mice", Journal of Immunology, vol. 126, pp. 1180-1184 (Mar. 1981).

Primary Examiner—Blondel Hazel
Attorney, Agent, or Firm—Scully, Scott, Murphy & Presser

[57] ABSTRACT

This invention provides a number of immunological reagents useful for the suppression of allergic reactions induced by Timothy-grass pollen allergen (or cross-reacting allergens thereof) and for methods of obtaining said reagents. The reagents include: (1) an anti-idiotypic antibody (anti-IgE$_{id}$) directed to the allergen (Timothy grass antigen) binding site of an IgE immunoglobulin; (2) an anti-idiotypic antibody directed to the allergenic T-cell helper factor ($T_{HF}$) derived from Timothy grass pollen antigen stimulated lymphocytes; (3) unique methods for generating antigen-specific T-suppressor cells ($T_S$); (4) a unique method for producing antigen-specific suppressor T cell factors ($T_{SF}$); (5) a method for fractionation of $T_{SF}$; and (6) a specific T cell factor, $T_{SF2}$. The invention further provides pharmaceutical compositions comprising the above anti-idiotypic antibodies or suppressor factor derived from $T_s$ cells.

29 Claims, No Drawings

TIMOTHY GRASS ANTIGEN SPECIFIC ANTI-IDIOTYPIC ANTIBODIES

BACKGROUND OF THE INVENTION

The nature of the allergic reaction or response in humans and animals to various antigens is not completely understood. It is theorized that the allergic response to a foreign antigen, such as the antigen of grass pollen, involves the interaction of at least two different cell types. One of these is conventionally termed a T-cell, or Thymus derived lymphocyte, and the second a B-cell, which is a bone marrow derived lymphocyte. Each of these two cells, the T and the B lymphocytes, recognize different parts of the antigenic protein that causes the allergic response. The B-lymphocyte recognizes the antigenic determinant whereas the T-lymphocyte recognizes a different portion of the protein, termed a carrier determinant. The B-cells of an animal sensitive to the antigen, upon recognition of the antigenic determinant of the antigen, produce antibodies to the antigen which give rise to the allergic reaction or response. T-cells do not produce the circulating antibody that is involved in allergic responses, but regulate their production by the B-cells. One sub-population of T-cells which assists in making antibodies are the so-called helper T-cells ($T_H$ cells). They effectively cooperate or interact with the B-lymphocyte to produce antibodies. Another sub-population of T-cells, the suppressor T-cell ($T_S$ cells), effectively suppresses the action of helper T-cells so that they cannot participate with B-lymphocytes to produce antibodies. It is thought that the $T_S$ cells also act on the B-cells themselves to inhibit the formation of antibodies.

The allergenic antibody is produced by the B-cells, as noted above, after recognition of the antigenic determinant of the antigen. This determinant is a peptide segment of the antigen protein molecule. In Timothy grass pollen the whole allergenic antigen is conventionally referred to as antigen B. All other grass antigens cross reactive with antigen B possess the same antigenic determinant as antigen B.

The peptide segment of the antibody protein molecule which binds to the antigenic determinant is conventionally referred to as the idiotype or idiotypic determinant. This same idiotypic determinant also exists in T and B cells as receptors.

Unsuccessful attempts have been made in the past to inhibit the allergic response in animals sensitive to various allergenic antigens by enhancing the $T_S$ cell population in such animals or affecting the $T_H$ cell population thereof.

It is an object of the present invention to provide an anti-idiotypic antibody which is directed against Timothy grass antigen B- specific (or any cross reactive grass antigen-specific) antibody.

It is a further object of the invention to provide $T_S$ cells and suppressor factors derived therefrom which directly affect the ability of $T_H$-cells and B-cells to produce allergenic antibody to the grass antigens.

It is still a further object of the invention to provide a pharmaceutical composition and method for treatment of animals, including humans, sensitive to Timothy grass antigen and other grass antigens cross reactive therewith.

SUMMARY OF THE INVENTION

According to the present invention there is provided a method of preparing an anti-idiotypic antibody directed against (1) Timothy grass antigen B- and (2) cross reactive grass antigen-specific allergenic antibody, IgE. The anti-idiotypic antibody, anti-IgE$_{id}$, is specifically reactive with the idiotypic determinants on IgE and (1) antigen B- and (2) cross reactive grass antigen-specific T and B cells and is prepared by:

(1) immunizing a first animal species with a source of antigen B, (2) collecting sera from the immunized first animal species, (3) separating IgE from the sera, (4) immunizing a second animal species with the IgE, (5) collecting sera from the immunized second animal species, and (6) separating anti-IgE$_{id}$ antibody from the sera.

The present invention also provides a method of preparing an anti-idiotypic antibody directed against (1) Timothy grass antigen B- and (2) cross reactive grass antigen-specific allergenic T-helper factor, $T_{HF}$. The anti-idiotypic antibody, anti-$T_{HF}$, is specifically reactive with the idiotypic determinants on the $T_{HF}$ and (1) antigen B- and (2) cross reactive grass antigenspecific T and B cells and is prepared by:

(1) immunizing a first animal species with photooxidized antigen B in alum, (2) collecting $T_H$-cells from the immunized first animal species, (3) culturing the $T_H$-cells with a source of Timothy grass antigen B or cross reactive grass antigen, (4) separating T-helper factor $T_{HF}$ from the culture, (5) immunizing a second animal species with the T-helper factor, $T_{HF}$, (6) collecting sera from the immunized second animal species, and (7) separating anti-$T_{HF}$ antibody therefrom.

The invention also provides a method of producing (1) Timothy grass antigen B- and (2) cross reactive grass antigen-specific T suppressor cells, $T_S$, comprising:

(1) culturing anti-IgE$_{id}$ or anti-$T_{HF}$ with normal cells of an animal to induce the formation of $T_S$ cells in the culture, and (2) separating the $T_S$ cells from the culture.

The invention further provides a method of producing T suppressor cells, $T_S$, comprising:

(1) immunizing an animal species with photooxidized antigen B, and (2) collecting $T_S$ cells from the immunized animal species.

The invention provides a further method of producing T suppressor cells, $T_S$, comprising:

(1) immunizing an animal species with anti-IgE$_{id}$ or anti-$T_{HF}$, and (2) collecting $T_S$ from the immunized animal species.

The invention also provides a method of producing (1) Timothy grass antigen B- and (2) cross reactive grass antigen-specific suppressor T-cell factor, $T_{SF}$, by extraction from $T_S$. $T_{SF}$ is actually a mixture of at least two other proteins, designated $T_{SF1}$ and $T_{SF2}$. Only $T_{SF1}$ is Timothy antigen binding. $T_{SF2}$, while not antigen binding, will bind to the idiotype expressed in $T_{SF1}$ or $T_{HF1}$ or the Ig molecule itself.

The invention provides a further method for producing $T_{SF}$, comprising:

(1) culturing T suppressor cells, $T_S$, with antigen-IgE$_{id}$, anti-$T_{HF}$ or antigen B, and (2) separating $T_{SF}$ from the cell containing culture.

The invention provides an additional method of producing T suppressor cells, $T_S$, comprising:

(1) culturing $T_{SF}$ with normal cells of an animal species, and (2) separating $T_S$ from the normal cell containing culture.

The invention provides a method of fractionating $T_{SF}$ into separate factors $T_{SF1}$ and $T_{SF2}$ comprising subjecting $T_{SF}$ to affinity chromatography on an adsorbent comprising Timothy grass antigen D, on an inert carrier substrate which binds $T_{SF1}$.

According to the present invention there is also provided a pharmaceutical composition in unit dosage form for suppressing the allergic response of an animal sensitive to Timothy grass antigen B or a cross reactive grass antigen comprising an anti-allergic response effective amount of anti-IgE$_{id}$, anti-$T_{HF}$, $T_{SF}$, $T_{SF1}$ or $T_{SF2}$ and a pharmaceutically acceptable carrier.

The present invention also provides a method for suppressing the allergic response of an animal sensitive to Timothy grass antigen B or a cross reactive grass antigen comprising administering to the animal an anti-allergenic response effective amount of anti-Ig$_{id}$, anti-$T_{HF}$, $T_{SF}$, $T_{SF1}$ or $T_{SF2}$.

DETAILED DESCRIPTION OF THE INVENTION

It is to be understood by those skilled in the art that the term "animal" as used herein and in the appended claims includes humans.

The present invention is predicated on the following theory of immune response by induction of T-cell suppression. As noted above the $T_H$ (helper) cells interact with B-cells in a sensitive or "allergic" animal upon recognition of the carrier and antigenic determinants, respectively, of the grass antigen, to produce the allergic antibody IgE. Administration to the animal of anti-idiotypic antibodies: anti-IgE$_{id}$ or anti-$T_{HF}$ induces the formation in the animal of suppressor T-cells (i.e., $T_S$-cells). More specifically, the anti-idiotypic antibodies induce the formation of at least two sub-populations of suppressor T-cells, namely, $T_{S1}$ and $T_{S2}$ cells.

It is believed that the $T_{S1}$ cells secrete a protein factor ($T_{SF1}$) which binds the allergenic antigen itself by reaction with the allergenic determinant thereof.

Similarly, it is theorized that the $T_{S2}$ cells secrete a protein factor $T_{SF2}$ that binds with the idiotype receptors on the $T_H$ (helper) cells and B-cells, thereby inhibiting the recognition by the $T_H$ and B-cells of the antigen and, hence, also inhibiting the production thereby of allergenic antibody IgE.

Although any of the above-described anti-idiotypic antibodies or T-cell suppressor factors may be utilized to immunize a sensitive animal to allergic responses to Timothy grass antigen B or other grass antigens cross reactive therewith, it will be understood by those skilled in the art that the most advantageous immunization agents will comprise those derived from the animal(s) of the same species as that to be immunized. Since the immunization protocol usually comprises a series of immunizations over a long period of time, the more "foreign" the immunization protein, the more likely the prospect that the immune system of the animal will recognize the protein and produce antibodies directed against it. Accordingly, it is preferred to derive the anti-idiotypic antibody or suppression factor from animals or cells of animals of the same species as that to be immunized so as to produce non-immunogenic proteins. The whole suppressor cells ($T_S$) could not, of course, be administered to an animal of a species different from that from which the cells were derived since they would be rejected by the immunized animal.

It will also be understood by those skilled in the art that in the methods of production of anti-idiotypic antibodies, anti-IgE$_{id}$ and anti-$T_{HF}$, the second animal species immunized with IgE and $T_{HF}$ to produce the antibodies should preferably be different from the first animal species in which the IgE and $T_{HF}$ were produced in order to optimize production of the antibodies. In the case of producing anti-IgE$_{id}$ it is also preferred to include the step of hyperimmunization when producing the IgE.

It will be further understood by those skilled in the art that although the examples set forth hereinbelow utilize affinity chromatography to achieve separation of the various protein fractions produced by the methods of the invention, any conventional method for separating proteins may be utilized.

For reasons not completely understood, animals immunized with photooxidized antigen B (Ox-AgB, prepared according to the methods described in U.S. Pat. No. 4,256,732, the disclosure of which is incorporated herein by reference) adsorbed in alum produce $T_H$ cells from which $T_{HF}$ can be derived. If, however, the Ox-AgB is incorporated in Freund's complete adjuvant (FCA) and administered to the animal, $T_S$ cells are produced from which $T_{SF}$ can be derived.

The steps of culturing the various proteins, antibodies or factors with cells may, of course, be conducted according to any standard culturing technique.

The references hereinbelow and in the claims to antigens D, $D_1$, $D_2$, $D_3$, etc. are to the antigen fragments which make up the mixture conventionally termed Timothy grass antigen B (see U.S. Pat. No. 4,256,732 and U.S. Pat. No. 4,140,679, the disclosures of which are also incorporated herein by reference).

In the above-described method for producing $T_S$ cells by culturing the anti-idiotypic antibody with normal animal cells it is preferred to utilize normal spleen cells, etc. Where the $T_S$ cells are to be employed for producing factors for use in humans it is preferred to utilize peripheral blood lymphocytes as the normal cells.

T-cells ($T_H$ and $T_S$) may be derived from the spleens of immunized animals according to the method of Wysocki et al, Proc. Natl. Acad. Sci., Vol. 75, pg. 2844+ (1978), the disclosure of which is incorporated herein by reference.

The $T_{SF}$ factor is preferably derived from the $T_S$ cells by extraction. Preferably, a suspension of the $T_S$ cells are repeatedly frozen and thawed to burst the cell walls and release the $T_{SF}$ factor. The latter is preferably isolated from the mixture by affinity chromatography in an inert carrier substrate to which is bound antigen $D_1$.

Alternatively, the $T_{SF}$ may be produced by culturing the $T_S$ cells with either of the anti-idiotypic antibodies, anti-IgE$_{id}$ or anti-$T_{HF}$, or with antigen B at 37° C. for about 24 hours. The culture medium is preferably centrifuged and the cell-free supernatant subjected to affinity chromatography.

The $T_{SF}$ fraction may be subjected to affinity chromatography to separate it into $T_{SF1}$ and $T_{SF2}$ fractions utilizing an inert carrier substrate to which is bound antigen $D_1$ (AgD$_1$) The adsorbed fraction is $T_{SF1}$, which may be eluted with a variety of reagents (0.1 m molar antigen D, 3 molar KSCN in PBS buffer (pH 7.2), 0.1 molar glycine-HCl, pH3, etc.)

The non-adherent material contains $T_{SF2}$ which may be isolated by affinity chromatography on an inert carrier substrate to which is bound $T_{SF1}$. The adherent material is $T_{SF2}$ which may be eluted with a variety of reagents (3 molar KSCN in PBS buffer (pH 7.2), 0.1 molar glycine-HCl, pH 3, etc.).

The $T_{SF1}$ and $T_{SF2}$ factors may be recovered from the eluants by dialysis against PBS buffer (pH 7.2) and concentrated by negative pressure to a convenient level.

The $T_{SF1}$ and $T_{SF2}$ fractions may be cultured with normal animal cells such as spleen cells, human peripheral blood lymphocytes, etc. at 37° C. for 4 days to produce $T_{S1}$ and $T_{S2}$ cells, respectively. The $T_S$ cells may be recovered from the culture by affinity chromatography methods using antigen or $T_{SF1}$ coated petri dishes or paper discs. The thus produced $T_S$ cell population will provide 100% suppression of Timothy Ig response.

The pharmaceutical composition of the invention preferably contains from about 0.37 to 3.7 mg of either anti-IgE$_{id}$, anti-T$_{HF}$, T$_{SF}$, T$_{SF1}$ or T$_{F2}$. The active ingredients may be compounded with any of the conventional adjuvants and carriers suitable for intravenous or subcutaneous administration of proteins.

To provide immunization against primary and secondary responses to Timothy grass antigen and cross reactive grass antigens, the composition should be administered every one to three months, preferably about once a month.

The invention is illustrated by the following non-limiting examples:

EXAMPLE 1

Preparation of anti-IgE$_{id}$ and anti-T$_{HF}$

The following abbreviations are employed herein: AgB, antigen B; AgD, antigen D; anti-E$_{id}$, antiidiotypic antibody; anti-IgEm, rabbit anti-mouse timothy IgE, con a, concanavalin A; C.S. buffer, cacodylic-saline buffer; FCA, Freund's complete adjuvant; FCS, fetal calf serum; HEPES, N-2-hydroxyethylpiperazine-N'-2-ethanesulfonic acid; HF, helper factor; KLH, keyhold limpet hemocyanin; NRS, normal rabbit serum; OVA, ovalbumin; Ox-AgB, photooxidized antigen B; PBS, phosphate-buffered saline; PCA, passive cutaneous anaphylaxis; SF, suppressor factor; T$_H$ cells, helper T cells; T$_{HF}$, helper T cell factor; T$_S$ cells, suppressor T cells; T$_{SF}$, suppressor T cell factor; WST, extract of Timothy grass pollen.

Timothy grass pollen extract (WST), purified antigen D (AgD), AgB, and Ox-AgB were prepared as described in Malley, A., Baecher, L., Begley, D., and Forsham, A., Mol. Immunol. 16: 929 (1979); and Malley, A. and Harris, R. L., Jr., J. Immunol. 99: 825 (1967). (See also U.S. Pat. No. 4,256,732). Ovalbumin (OVA) was recrystallized three times. Antigen-B specific helper factor (T$_{HF}$) and suppressor factor (T$_{SF}$) were prepared according to the following methods.

Spleen cells from mice primed with Ox-AgB in alum were obtained 7 days after priming. A T cell enriched population was obtained by passage of these cells over nylon wool [Julius, M. H., Simpson, E., and Herzenberg, L. A., Eur. J. Immunol. 3: 645 (1973)], and the non-adherent T cell population was cultured with an optimum concentration of Ox-AgB for 5 to 18 hours at 37° in 5% CO$_2$ in air. The cell-free supernatant (CFS) was removed by centrifugation, and AgB-specific T$_{HF}$ was purified by affinity chromatography on Seph-AgD$_1$. The AgB-specific T$_{HF}$ was eluted from the adsorbent with 3 M KSCN in PBS, pH 7.2. The recovered T$_{HF}$ was applied to the Seph-AgD$_1$ adsorbent a second time, and greater than 95% of the protein bound was eluted with KSCN. As little as three micrograms of protein of the isolated AgB-specific T$_{HF}$ injected intravenously with a limiting number (2.5×10$^6$) of WST-primed B cells (anti-thy plus complement treated) induces a secondary IgE response with a titer of 3,000 in syngeneic x-irradiated (650 rads) recipients.

AgB-specific T$_{SF}$ was obtained by sonication of spleen cells from mice primed with Ox-AgB in FCA. The CFS was collected by ultracentrifugation at 20,000 rpm for 20 min., and AgB-specific T$_{SF}$ was isolated by passage twice over a Seph-AgD$_1$ affinity adsorbent (6). Ten micrograms (10 μg of protein) of AgB-specific T$_{SF}$ completely suppresses a secondary anti-timothy IgE response.

LAF$_1$ mice, 8 to 12 weeks old, were immunized with WST as described in Fairchild, S., and Malley, A., J. Immunol. 115: 446 (1975); and Fairchild, S. and Malley, A., J. Immunol. 117: 2137 (1967). For the production of T$_H$ cells, mice were immunized once intraperitoneally with 150 μg of Ox-AgB adsorbed on 1 mg of alum, and 7 days later single-cell preparations of their spleens were made as described in Fairchild et al, supra. Suppressor T cells were obtained from mice primed with 150 μg of Ox-AgB incorporated in FCA twice at 14-day intervals; the spleen cells were collected 7 days later.

Mice immunized with OVA received 10 μg injections of OVA protein adsorbed on 1 mg of alum, and the spleen cells were collected 7 to 10 days later.

Rabbit anti-helper factor was prepared by immunization of albino New Zealand rabbits with 150 μg of protein of affinity-purified AgB-specific T$_{HF}$ in FCA distributed in 3 to 4 sites along the backs of the rabbits. Each rabbit received a booster injection of the same amount of T$_{HF}$ in FCA at 12- to 18-day intervals over the next 50 days, and the animals were exsanguinated 7 days after the last injection of T$_{HF}$.

Anti-IgE$_m$ was prepared as described by Malley, A., Begley, D., and Forsham, A., Immunol. Commun. 6: 473 (1977), and the specific antibody (anti-E$_{id}$) was separated from anti-IgE$_{Fc}$ (heavy-chain-specific) antibodies by affinity chromatography (described below).

Rabbit anti-T-helper factor and rabbit anti-E$_{id}$ antisera were routinely passed over Sepharose rabbit anti-mouse Ig and Sepharose-fetal calf sera (Seph-FCS) adsorbents to remove any nonspecific antibodies present in these antisera.

Spleen cells or nylon wool enriched T cells from mice primed with Ox-AgB in alum or FCA, and OVA in alum, were cultured for 5 days at 37° C. in 5% CO$_2$ in air as described by Fairchild, supra, and Fairchild, S. and Malley, A., J. Immunol. 117: 2137 (1967). Cultures received pulses of $^3$H-thymidine (1 μCi; 6.7 mmol/Ci, New England Nuclear, Gardena, Cal.) during the last 24 hours of culture. Upon termination of these cultures the cells were harvested by a minimultiple automatic sample harvester (Microbiological Associates, Los Angeles, Cal.), and harvested samples were counted on a Packard scintillation counter (Packard Instrument Company, Inc., Downers Grove, Ill.).

In experiments to block antigen-induced proliferation, whole spleen cells or nylon wool enriched T cells cultured with antigen (AgB or OVA) were preincubated for 90 min. at 37° C. with 750 μl of anti-$T_{HF}$ serum, 150 μl of anti-Eid serum, or 750 μl of normal rabbit serum (NRS). The cells were washed 3 times with RPMI 1640 supplemented with N-2-hydroxyethyl-piperazine-N'-2-ethanesulfonic acid (HEPES) buffer, 5% fetal calf serum (FSC) and penicillin-streptomycin (100 units/ml). These cells were diluted to 2 ml with the same media for a final dilution of $6 \times 10^6$ cells/ml. One hundred microliters of these cell suspensions were added to each well of a Falcon micro-titer plate (Falcon Labware Division, Becton Dickinson, Oxnard, Cal.), and 5 μg of AgB (100 μl), 0.5 μg of concanavalin A (con A) (100 μl), or 5 μg of OVA (100 μl were added and these mixtures were cultured for 5 days as described above.

The ability of anti-$T_{HF}$ or anti-$E_{id}$ to induce proliferation of $T_H$ and $T_S$ cells was determined by culturing nylon wool nonadherent T cells from mice primed with Ox-AgB in alum or cells from mice primed with Ox-AgB in FCA and enriched for T cells by the method of Wysocki et al, supra.

Spleen cells from mice immunized with WST were either passed over nylon wool to provide immune T cells or were treated with rabbit anti-thy 1.2 (1:40 final dilution at 4° C. for 1 hr) and guinea pig complement (1:10 final concentration) (Colorado Serum Company, Denver, Colo.) to provide immune B Cells.

Previous studies have demonstrated that intravenous injection of a limiting number of immune B cells ($2.5 \times 10^6$ cells) and $4 \times 10^6$ immune T cells into X-irradiated (600 rads) syngeneic mice and subsequent challenge with 10 μg of WST in alum within 2 hours initiated a significant secondary IgE response. Serum IgE was measured by PCA in Sprague-Dawley rats according to the method of Fairchild, S. and Malley, A., J. Immunol. 115: 446 (1975), and IgG was measured by a modified radioimmunoassay as described by Malley, A, Begley, D. C., and Forsham, A., Int. Arch. Allergy Appl. Immunol., 62: 276 (1980).

The ability of anti-idiotypic antibodies to block or enhance $T_H$ or B cell activity was determined through incubation of $T_H$ or B cells ($2 \times 10^7$ cells) with 1 ml of anti-$T_{HF}$ (diluted 1:2.5 in unsupplemented RPMI), 1 ml of anti-$E_{id}$ (diluted 1:5 in unsupplemented RPMI) or 1 ml of NRS (diluted 1:2.5 in unsupplemented RPMI) for 90 min. at 37° C. The cell suspensions were washed 3 times in RPMI, mixed with the appropriate quantity of untreated immune T or B cells, and injected intravenously into X-irradiated (600 rads) syngeneic recipients.

The AgD fragment of timothy grass pollen was attached to Sepharose-AH-4B (Pharmacia Fine Chemicals, Piscataway, N. J.) as described by Malley, A., Baecher, L., and Begley, D., Immunochemistry 12: 551 (1975) and Malley, A., Baecher, L., and Begley, D., Dev. Biol. Stand. 29: 29 (1975). Antigen-B-specific $T_{HF}$ and $T_{SF}$ were partially purified by passage of the cell-free supernatant fluids containing either $T_{HF}$ or $T_{SF}$ over the Sepharose-AH-AgD (Sepharose-AgD) adsorbent. Nonadherent proteins were washed off with excess 0.01 M cacodylicsaline (C.S.) buffer, pH 7. Bound proteins were eluted with 3 M KSCN in C.S. buffer. Eluted proteins were dialyzed against phosphate-buffered saline (PBS) and concentrated by negative pressure.

Antigen B was attached to Sepharose 4B by the method of March et al, Ann. Biochem. 60: 149 (1978). The Sepharose-AgB adsorbent was treated with 3 ml of mouse anti-AgB IgE serum diluted to 10 ml with C.S. buffer. The IgE titer of this antiserum was 1:60,000 measured by PCA in Sprague-Dawley rats. When all of the diluted anti-AgB IgE serum was on the adsorbent, the flow was stopped and this suspension was incubated at room temperature for 2 hours. The adsorbent (10 ml of packed Sepharose) was washed with 500 ml of C.S. buffer to remove nonspecifi-cally bound protein. The first 100 ml of this wash was recovered and reconcentrated for recovery of unbound anti-AgB IgE antibodies. The Sepharose AgB-IgE complex was next treated with 0.02 M gluteraldehyde for 60 min. at room temperature to stabilize the bound IgE to the AgB. The Sepharose AgB-IgE adsorbent was washed with 250 ml of C.S. buffer, 50 ml of 3 M KSCN in C.S. buffer, 200 ml of distilled water, and 200 ml of each of the following reagents: 0.5 M $Na_2CO_3$-0.5 M NaCl, pH 10; 1 M NaAc-0.5 M NaCl, pH 4.0; 2 M urea-0.5 M NaCl; and C.S. buffer, pH 7.0.

The anti-$IgE_m$ was separated into heavy-chain-specific (anti-$IgE_{Fc}$) and anti-Eid antibodies by passage over the Sepharose AgB-IgE adsorbent. The anti-$IgE_m$ antibodies were precipitated with ammonium sulfate as described by Campbell et al, Methods in Immunology, W. A. Benjamin, Inc., New York, N.Y., p. 118 (1963), and the final precipitate was dialyzed extensively against C.S. buffer and concentrated by negative pressure. The protein concentration of the IgG preparation was determined spectrophometrically on the basis of the extinction coefficient of rabbit IgG, $E_{280}^{1\%} = 14.5$. Approximately 12 mg of protein (0.4 ml) of the IgG fraction of rabbit anti-$IgE_m$ was applied to the Sepharose AgB-IgE fraction of rabbit anti-$IgE_m$ was applied to the Sepharose AgB-IgE adsorbent in C.S. buffer. The nonadherent protein was eluted with C.S. buffer, and bound protein was eluted with 3 M KSCN in C.S. buffer. Upon dialysis and concentration, nonadherent and eluted fractions were assayed for their ability to neutralize AgB-specific IgE or OVA-specific IgE (a gift from Schering Company, West Germany). The fraction eluted from the Sepharose AgB-IgE adsorbent with KSCN was equally efficient in neutralizing AgB and OVA-specific IgE antibodies, and is therefore referred to as anti-$IgE_{Fc}$. The fraction not adhering to the Sepharose AgB-IgE adsorbent was effective in neutralizing AgB-specific IgE but not OVA-specific IgE antibodies and is therefore referred to as anti-$E_{id}$.

Attempts to conjugate affinity-purified AgB-specific $T_{HF}$ or $T_{SF}$ to Sepharose or affi-gel 10 (Bio-Rad Laboratories, Richmond, Cal.) and to have the conjugated factor retain its ability to react with antigen or anti-idiotypic antibodies were unsuccessful. However, pre-incubation of AgB-specific $T_{SF}$ with soluble antigen for 1 to 2 hours at 37° C. prior to coupling with affi-gel 10 provided an insolubilized AgB-specific TSF adsorbent that could be used to purify anti-idiotypic antibody. Antigen-B-specific $T_{SF}$ (500 μg of protein) was incubated with 25 mg of AgD at what was calculated to be about equal molar quantities. After incubation for 60 min. at 37° C. the solution was added to 12 g of affi-gel 10 equilibrated in 0.1 M $NaHCO_3$ (pH 8), and the suspension was stirred at room temperature for 6 hours and overnight at 4° C. The suspension was centrifuged at 2,500 rpm for 20 min. at 4° C. to remove the supernatant. The affi-gel matrix was washed in 0.1 M $NaHCO_3$ buffer (pH 8) and resuspended in 1 M ethanolamine (Mallinckrodt, Inc., St. Louis, Mo.) in 0.1 M NaHCO$_3$, ph 8. The suspension was stirred at room temperature for 1 hour and then washed 3 times in C.S. buffer. The washed adsorbent was treated with 3 M KSCN in C.S. buffer for 30 min. to remove AgD$_1$ bound to the T$_{SF}$ and any free or weakly bound proteins. The excess KSCN was removed from the T$_{SF}$-affi-gel adsorbent by extensive washing in C.S. buffer and stored at 4° C. until ready for use.

Fetal calf serum (Grand Island Biological Company, Santa Clara, Cal.) was attached to Sepharose 4B by the method of March et al, supra. The Sepharose-FCS adsorbent was used to evaluate the specificity of anti-T$_{HF}$ and anti-E$_{id}$ binding to an AgB-specific T$_{SF}$ affinity adsorbent.

The possibility that anti-T$_{HF}$ serum contained anti-idiotypic antibody activity was examined with T cells from mice primed with Ox-AgB in alum preincubated with NRS, anti-T$_{HF}$, or anti-E$_{id}$ for 90 mi-. at room temperature. Preincubation of AgB-specific T$_H$ cells with NRS did not reduce the ability of these cells to respond to either AgB or con A. Preincubation of these cells with either anti-T$_{HF}$ or anti-E$_{id}$ completely blocked their ability to respond with AgB, but did not reduce the level of $^3$Hthymidine incorporation of these cells by con A. Specificity of the effect of anti-T$_{HF}$ and anti-E$_{id}$ was demonstrated by the failure of these antibodies to block either con A or OVA-induced proliferation responses with OVA/al-primed cells (Table 1). Spleen cells from nonimmunized mice pretreated with either anti-T$_{HF}$ or anti-E$_{id}$ did not respond when cultured with AgB or OVA, but gave normal levels of $^3$H-thymidine incorporation with con A.

lower than that used to block proliferation of T$_H$ cells (Table 1).

Since anti-T$_{HF}$ and anti-E$_{id}$ initiated significant levels of $^3$H-thymidine incorporation with AgB-specific T$_H$ cells, it was determined if the action of anti-T$_{HF}$ and anti-E$_{id}$ antisera upon either T$_H$ cells or immune B cells (primed with WST and treated with anti-thy 1.2 and complement) would enhance the secondary AgB-specific IgE response in X-irradiated recipients (Table 2). Immune T cells (nonadherent to nylon wool) from WST-primed mice mixed with immune B cells at a limiting ratio gave a good secondary IgE response. Preincubation of either T$_H$ or B cells with NRS did not alter the secondary IgE response in the irradiated recipients. On the other hand, preincubation of either T$_H$ or B cells with anti-T$_{HF}$ or anti-E$_{id}$ antisera significantly enhanced the secondary IgE response in the irradiated recipients. The level of enhanced antibody formation obtained by pretreatment with anti-E$_{id}$ was slightly less than that achieved with OVA-primed T cells (nylon wool nonadherent) or B cells (anti-thy and complement) did not alter their immune response in X-irradiated syngeneic recipients. The AgB-specific IgG antibody response in all of the groups tested was less than the sensitivity of the radioimmunoassay (100 ng/ml).

TABLE 1

Effect of pretreating ovalbumin- and photooxidized-antigen-B-primed cells with anti-antigen B idiotypic antisera upon the antigen-specific lymphocyte transformation response.

| Source of spleen cells | Treatment[a] | $^3$H—thymidine incorporation[b] | | |
|---|---|---|---|---|
| | | AgB | Con A | OVA |
| Ox—AgB-primed[c] | NRS | 47,521 ± 1,125 | 39,758 ± 1,102 | 1,075 ± 500 |
| | anti-T$_{HF}$ | 910 ± 310 | 40,150 ± 1,275 | 1,210 ± 250 |
| | anti-E$_{id}$ | 1,170 ± 450 | 39,927 ± 1,151 | 975 ± 390 |
| Ova-primed[d] | NRS | 975 ± 250 | 37,521 ± 1,395 | 32,175 ± 1,161 |
| | anti-T$_{HF}$ | 1,210 ± 300 | 39,357 ± 1,510 | 35,193 ± 1,710 |
| | anti-E$_{id}$ | 1,157 ± 291 | 39,771 ± 2,100 | 34,710 ± 1,423 |

[a]Nylon wool enriched T cells from mice primed with either OVA or Ox—AgB were preincubated for 90 min. at 37° C. with 750 μl of heat-inactivated anti-T$_{HF}$, NRS, or 150 μl of anti-E$_{id}$. The cells were washed 3 times with 5%-FCS-supplemented RPMI 1640 media, and resuspended to a final volume of 2 ml.
[b]Cell suspensions, at a final concentration of 6 × 10$^6$ cells/ml, were cultured with 100 μl of each cell preparation and the optimal concentrations of AgB (10 μg of protein), con A (0.5 μg of protein). The values reported are the means of triplicate cultures ± SD and are corrected for background.
[c]Animals were immunized with 150 μg of Ox—AgB adsorbed on 1 mg of alum. Spleens were collected 7 days later, and 2 × 10$^8$ cells were passed over nylon wool columns.
[d]Animals were immunized with 10 μg of OVA adsorbed on 1 mg of alum. Spleens were collected 7 days later, and 2 × 10$^8$ cells were passed over nylon wool columns.

The direct proliferative effect of anti-T$_{HF}$ and anti-E$_{id}$ antisera upon AgB-specific T$_H$ and T$_S$ cells is shown in FIG. 1. Nylon wool nonadherent T cells from mice primed with Ox-AgB in alum provided a source of T$_H$ cells. T cells enriched by depleting B cells on petri dishes coated with goat anti-mouse Ig (provided by National Institute for Medical Research, Mill Hill, England) from mice primed with Ox-AgB in FCA provided a source of T$_S$ cells. Both T$_H$ H and T$_S$ S populations contained less than 5% cells that stained with fluorescein-anti-mouse Ig (Micro-biological Associates, Los Angeles, Cal.). Both T$_H$ and T$_S$ cells show significant levels of $^3$H-thymidine incorporation at concentrations of anti-T$_{HF}$ and anti-E$_{id}$ that are 20 to 50 times

TABLE 2

Enhancement of the antigen-B-specific IgE response by pretreatment of immune cell populations with anti-idiotype.

| Treatment[a] | Cell population[b] treated | Ratio of cells given recipients[c] | IgE response[d] |
|---|---|---|---|
| None | — | T/B 4 × 10$^6$/2.5 × 10$^6$ | 600 |
| NRS | T | | 600 |
| anti-T$_{HF}$ | T | 4 × 10$^6$/2.5 × 10$^6$ | 2,800 |
| anti-E$_{id}$ | T | | 1,600 |
| NRS | B | | 600 |
| anti-T$_{HF}$ | B | 4 × 10$^6$/2.5 × 10$^6$ | 3,200 |

TABLE 2-continued

Enhancement of the antigen-B-specific IgE response by pretreatment of immune cell populations with anti-idiotype.

| Treatment[a] | Cell population[b] treated | Ratio of cells given recipients[c] | IgE response[d] |
|---|---|---|---|
| anti-E$_{id}$ | B | | 1,600 |

[a]Cell populations (T or B cells) were treated with 1.5 ml of heat-activated NRS or anti-T$_{HF}$ and 1.0 ml of anti-E$_{id}$ per $2 \times 10^7$ cells. These mixtures were rocked at 37° C. for 90 min. and centrifuged at 1,000 rpm for 10 min.; the supernatant was discarded. The cell pellets were resuspended in PBS and washed 2 more times with PBS before being resuspended to a final volume of $2 \times 10^7$ per ml.
[b]Spleen cells from mice immunized with 10 μg of protein of WST adsorbed on 1 mg of alum at 21-day intervals were collected on day 28. Single-cell suspensions were prepared; portions of these cells ($2 \times 10^8$ cells) were passed over nylon wool columns and represent immune T cells (not adherent to nylon wool). The remaining cells, treated with anti-thy 1.2 (L:10) and complement (1:10), represent immune B cells.
[c]Syngeneic recipients were X-irradiated (600 rads) and received intravenous injections of $4 \times 10^6$ T cells and $2.5 \times 10^6$ B cells. All recipients were challenged within 2 hrs. of this injection with 10 μg of WST.
[d]Passive cutaneous anaphylaxis responses were determined in duplicate in Sprague-Dawley rats. The values represent the mean reactions observed in at least 2 rats. At least 3 animals per group made up the serum pool tested, and blood was collected 7, 10 and 14 days after cell transfers. The titer reported represents the mean titer of the maximum response (day 7) observed.

Purification of anti-idiotypic antibodies by affinity chromatography was achieved with an AgB-specific T$_{SF}$-affi-gel adsorbent (affi-gel 10$_{SF}$). Fractions of anti-T$_{HF}$ or anti-E$_{id}$ eluted from the affi-gel-T$_{SF}$ with KSCN in PBS (pH 7.2) retained their ability to initiate $^3$H-thymidine incorporation when cultured with spleen cells from mice primed with either WST or Ox-AgB in alum (Table 3). These same fractions were inactive (background levels of $^3$H-thymidine incorporation) in cultures with normal spleen cells (data not shown). The elute fraction of NRS (1:5) applied to affi-gel-T$_{SF}$ adsorbent was also inactive. The anti-idiotypic antibodies present in anti-T$_{HF}$ antiserum did not bind nonspecifically to either a Sepharose-FCS adsorbent (Table 3) or an affi-gel adsorbent saturated with 1 M ethanolamine.

TABLE 3

Purification of anti-idiotypic antibodies on an antigen-B-specific T suppressor factor affi-gel affinity adsorbent.

| Sample | Adsorbent | Fraction[a] | Volume tested (μl) | $^3$H—thymidine incorporation[b] (CPM ± SD) |
|---|---|---|---|---|
| anti-T$_{HF}$ (1:5) | Seph-FCS | column | 10 | 13,160 ± 875 |
| | | pass | 50 | 28,190 ± 2,045 |
| | | | 100 | 21,200 ± 2,127 |
| anti-T$_{HF}$ (1:5) | Seph-FCS | eluate | 10 | 322 ± 362 |
| | | | 50 | 590 ± 319 |
| | | | 100 | 965 ± 475 |
| normal rabbit serum (1:5) | affi-gel | eluate | 10 | 375 ± 290 |
| | | | 50 | 497 ± 418 |
| | | | 100 | 921 ± 510 |
| anti-T$_{HF}$ (1:5) | affi-gel T$_{SF}$ | eluate | 10 | 26,009 ± 2,153 |
| | | | 50 | 36,240 ± 1,741 |
| | | | 100 | 29,959 ± 1,915 |
| anti-T$_{HF}$ (1:5) | affi-gel T$_{SF}$ | column | 10 | 435 ± 275 |
| | | pass | 50 | 543 ± 295 |
| | | | 100 | 595 ± 280 |
| anti-E$_{id}$ (1:5) | affi-gel T$_{SF}$ | eluate | 10 | 8,975 ± 1,201 |
| | | | 50 | 15,375 ± 975 |
| | | | 100 | 11,811 ± 917 |
| anti-E$_{id}$ (1:5) | affi-gel T$_{SF}$ | column | 10 | 515 ± 195 |
| | | pass | 50 | 621 ± 250 |
| | | | 100 | 710 ± 235 |

[a]One-to five-milliliter portions of anti-T$_{HF}$, anti-E$_{id}$, or normal rabbit antiserum were applied to 10-to 15-ml packed volumes of the indicated affinity adsorbents. The column pass (nonadherent) and eluate (adherent) fractions were dialyzed against PBS, pH 7.2, and concentrated by negative pressure back to their original volume.
[b]Cell suspensions, at a final concentration of $6 \times 10^6$/ml, were cultured with 100 μl and the indicated volumes of antisera. RPMI 1640 medium supplemented with 5% fetal calf serum was added to each well for a final volume of 200 μl/well. The values reported represent the means of triplicate cultures ± SD and are corrected for background.

EXAMPLE 2

Regulation of primary and secondary anti-AgB-specific IgE responses with anti-idiotypic antibodies.

The data hereinbelow indicates that both anti-idiotypic antibodies suppress AgB-specific IgE responses, the suppression lasting for at least 35 days, and being mediated by a thy $1^+$Lyt $1^-23^+$ T cell.

Timothy pollen extract (WST), purified antigen B (AgB), phooxidized antigen B (Ox-AgB), and AgB-specific T$_{SF}$ were prepared as described above.

CBA/Ca by C57BL6 F$_1$ mice and Sprague-Dawley rats were bred under specific pathogen-free conditions at the National Institute for Medical Research, Mill Hill, London. In most experiments male mice 9 to 12 weeks old and rats weighing 200 to 250 g were used.

Animals treated with WST were injected intraperitoneally (i.p.) with 10 μg of protein of WST adsorbed on 1 mg of alum on day 0. Animals given a secondary antigen challenge were treated with the same dose of WST in alum on day 21.

Normal mice were injected with affinity-purified normal rabbit IgG (nRGG), anti-T$_{HF}$, or anti-IgE$_{id}$ from 0.1 to 10 μg of protein per day for 3 successive days. Twenty-four hours later immunized animals were primed with 10 μg of protein of WST adsorbed on 1 mg of alum and 21 days later these animals were given a secondary boost with the same dose of WST.

The indiction of anti-ovalbumin IgE responses was achieved by injecting animals with 10 μg of protein ovalbumin (OVA) absorbed on 1 mg of alum.

The Fab$_2$ fragments of anti-T$_{HF}$ were prepared by pepsin digestion of the intact anti-T$_{HF}$ antibody at pH 4.2 [Williams, C. A., and Chase, M. W., Academic Press, 1: 422 (1967]. The digest was then passed over a protein-A-Sepharose adsorbent to remove intact undigested antibodies and Fc fragments present in the digest. The effluent not adherent to the protein-A-Sepharose adsorbent was concentrated by negative pressure against PBS buffer to a concentrate of 0.84 mg of protein/ml. Normal rabbit IgG was purified from normal rabbit serum by passage of rabbit serum over a protein-A-Sepharose adsorbent. The sample bound to the adsorbent was eluted with 3 M KSCN in PBS buffer, pH 7.2. The eluted fraction was concentrated by negative pressure against PBS buffer, pH 7.2, to a final concentration of 2.5 mg of protein/ml, and gave a single precipitin band against anti-normal rabbit sera and anti-rabbit IgG.

The anti-Thy 1.2 antiserum was monoclonal antibody prepared at the National Institute for Medical Research (NIMR), Mill Hill, London, England (designated NIMR-1), and goat anti-mouse Fab antisera was obtained from NIMR, Mill Hill, London.

Spleen cells from animals treated with either normal rabbit IgG or anti-$T_{HF}$ were removed under aseptic conditions, washed in PBS, and varying amounts of these cells were injected intravenously into recipient animals. All recipient animals had been primed 20 days earlier with 10 μg of protein of WST adsorbed on 1 mg of alum, and received a secondary boost of the same dose of antigen within 24 hours after cell transfer. In some experiments donor cells were treated with either normal rabbit serum or anti-Thy 1.2 antiserum and complement before the washed cells were injected into recipient animals.

The method of Wysocki et al, supra, was used to obtain a population of enriched T cells from spleen cell populations. Briefly, plastic-coated petri dishes were coated with anti-mouse Fab antibody and $3 \times 10^7$ spleen cells (in 3 ml) were incubated per dish at 4° C. for 60 min. Nonadherent cells were removed by Pasteur pipette and the coated dishes washed with 7 ml of cold buffer. The combined wash and initial aliquot of nonadherent cells were washed several times in cold buffer and represent a T-enriched cell population. Analysis of the nonadherent cell population indicated that this cell population was between 2 and 5% Ig+ when examined by fluorescein-conjugated anti-mouse Ig sera, and at least 95% Thy-1+ when stained with fluorescein-conjugated anti-Thy-1 antisera.

The serum IgE titers were measured by passive cutaneous anaphylaxis (PCA) [Moto et al, Life Science, 8: 813 (1969) and Fairchild et al, J. Immunol. 115: 446 (1975)] with 500 μg of WST in phosphate-buffered saline (PBS) as the antigen challenge. The PCA titer was measured in duplicate in Sprague-Dawley rats and is expressed as the reciprocal of the highest dilution of serum yielding a 5-mm (diameter) bluing reaction.

Sepharose adsorbents coupled with normal mouse serum (NMS), the F(ab)₂ fragments of mouse IgG, and AgB-specific $T_{HF}$ were described above in Malley et al, Immunol. Commun. 6: 473 (1977) Protein-A-Sepharose adsorbent was purchased from Pharmacia (Piscataway, N.J.).

Pretreatment of normal mice with nRGG for 3 successive days prior to immunization with 10 μg of protein of WST adsorbed on 1 mg of alum did not alter the normal primary or secondary response to WST (Table 4). On the other hand, pretreatment with either anti-$T_{HF}$ or anti-IgE$_{id}$ completely suppressed a primary WST response, and yielded a dose-related suppression of the secondary WST response (Table 5). The suppression induced by anti-$T_{HF}$ or anti-IgE$_{id}$ pretreatment persists at least 35 days. The observed suppression could be due either to the induction of a population of suppressor T cells or by antibody feedback suppression. In experiments to distinguish between these two possibilities, we found that cells from mice injected with nRGG and treated with either NRS or anti-thy 1.2 and C' did not alter the secondary anti-AgB IgE response. However, cells obtained from mice injected with anti-$T_{HF}$ and treated with NRS and C' suppressed the secondary anti-AgB IgE response, but treatment of these cells with anti-thy 1.2 and C' completely abrogated the observed suppression. This suggests that the reduction in anti-AgB IgE antibody by anti-$T_{HF}$ treatment was mediated by a population of suppressor T ($T_S$) cells.

TABLE 4

The effect of pretreatment of normal mice with anti-idiotypic antibody upon the primary and secondary anti-timothy IgE responses.

| Treatment[a] | Dose g/day | Primary IgE response[b] | | Secondary IgE response[b] | |
|---|---|---|---|---|---|
| | | day 7 | day 19 | day 7 | day 14 |
| normal rabbit IgG | 10.0 | 50 | 100 | 800 | 600 |
| anti-$T_{HF}$ | 0.1 | — | — | 400 | 200 |
| anti-$T_{HF}$ | 1.0 | — | — | 200 | 100 |
| anti-$T_{HF}$ | 10.0 | — | — | 200 | 100 |
| anti-IgE$_{id}$ | 0.1 | — | — | 400 | 200 |
| anti-IgE$_{id}$ | 1.0 | — | — | 400 | 100 |
| anti-IgE$_{id}$ | 10.0 | — | — | 200 | 100 |

[a]Affinity purified normal rabbit IgG (nRGG), anti-$T_{HF}$, or anti-IgE$_{id}$ was injected intravenously at the indicated doses for three successive days (−3 to −1) into six normal mice per group. All animals were challenged with 10 μg of protein of WST adsorbed on 1 mg of alum on day 0, and given a secondary boost with the same dose of WST on day 21.

[b]IgE responses were measured by passive cutaneous anaplylaxis (PCA) in Sprague-Dawley rats. All titrations were done in triplicate and the values represent the reciprocal of the mean of the lowest dilution giving a 5 × 5 positive reaction.

TABLE 5

Evidence of anti-idiotypic antibody induction of T cells that suppress a secondary anti-timothy IgE Response

| Immunization[a] | Donor cell treatment[b] | IgE response[c] | | |
|---|---|---|---|---|
| | | Day 7 | 11 | 14 |
| normal rabbit IgG | NRS + C' | 1600 | 1200 | 800 |
| | anti-Thy + C' | 1600 | 1200 | 800 |
| anti-$T_{HF}$ | NRS + C' | 200 | 100 | 100 |
| | anti-Thy + C' | 1600 | 1200 | 800 |

[a]Normal mice were injected with 10 μg of protein of either normal rabbit IgG or affinity purified anti-$T_{HF}$ daily for 3 days. On day 4 the spleens were removed and single-cell suspensions made.

[b]Cell suspensions were treated with equal volumes of either normal rabbit sera (NRS) or anti-Thy 1.2 sera and guinea pig complement (C') at a 1:3 dilution for 1 hour at 37° C. Donor cells, after treatment with NRS or anti-Thy 1.2 and C', were washed twice with PBS and $2.5 \times 10^7$ cells were injected intravenously into six recipient mice per group. Recipients had been primed 20 days earlier with 10 μg of protein of WST on 1 mg of alum. Twenty-four hours after cell transfer, all mice received a secondary WST challenge (10 μg of protein in alum).

[c]IgE responses were measured by PCA in Sprague-Dawley rats. All titrations were done in duplicate and the values represent the reciprocal of the mean of the lowest dilution giving a 5 × 5 mm positive reaction.

Further evidence that the observed suppression is mediated by a $T_S$ cell population is shown by Table 6. Animal given cells from mice treated with nRGG and nonadherent to goat anti-mouse-Ig-coated petri dishes did not alter a secondary anti-AgB response. Animals given cells from mice treated with anti-$T_{HF}$ and nonadherent to goat anti-mouse-Ig-coated petri dishes significantly suppressed (>90%) a secondary anti-AgB IgE response, and as little as 10⁶ of the enriched T cells transferred into primed recipients resulted in a 75% suppression of the secondary response.

TABLE 6

Titration of cells non-adherent on goat anti-mouse Ig—(Fab)-coated petri dishes.

| Immunization[a] | Number of cells transferred | Number of recipients[b] | IgE response[c] Day | |
|---|---|---|---|---|
| | | | 7 | 14 |
| anti-$T_{HF}$ | $4 \times 10^7$ | 6 | 200 | 0 |
| | $10^7$ | 6 | 300 | 0 |
| | $5 \times 10^6$ | 6 | 400 | 0 |
| | $10^6$ | 6 | 400 | 0 |
| | $5 \times 10^5$ | 4 | 800 | 200 |
| | $10^5$ | 4 | 1,600 | 400 |

TABLE 6-continued

Titration of cells non-adherent on goat anti-mouse Ig—(Fab)-coated petri dishes.

| Immunization[a] | Number of cells transferred | Number of recipients[b] | IgE response[c] Day 7 | 14 |
|---|---|---|---|---|
| nRGG[d] | $3 \times 10^7$ | 6 | 1,600 | 400 |

[a] Animals were injected intravenously with 10 μg of protein of either anti-T$_{HF}$ or nRGG daily for three days. Twenty-four hours later spleens were removed and applied to goat-anti-mouse Ig—(Fab)-coated plates at 4° C. Nonadherent cells were recovered, washed twice with PBS, and resuspended in PBS.
[b] All recipients were primed twenty days earlier with 10 μg of protein of WST adsorbed on 1 mg of alum. The indicated number of cells non-adherent to the goat-anti-mouse Ig plates were injected intravenously and within 24 hours all recipients were given a secondary WST challenge.
[c] IgE response was measured in duplicate by PCA in Sprague-Dawley rats. The mean titer is reported.
[d] nRGG - normal rabbit gamma globulin.

Specificity of the suppression induced by anti-T$_{HF}$ treatment is shown by Table 7. Animals treated with anti-T$_{HF}$ and immunized with 10 μg of ovalbumin adsorbed on 1 mg of alum have the identical primary IgE response as control animals treated intravenously with saline and then immunized with ovalbumin.

TABLE 7

Effect of anti-T$_{TF}$ antibody treatment upon the induction of anti-ovalbumin IgE formation.

| Immunization[a] | Treatment[b] | Number of animals | IgE Response[c] Day 7 | 10 | 14 |
|---|---|---|---|---|---|
| OVA | none | 4 | 800(600–1200) | — | 400(100–600) |
| OVA | anti-T$_{HF}$ | 4 | 800(600–1200) | — | 400(100–600) |

[a] All animals were immunized intraperitoneally with 10 μg of ovalbumin adsorbed on 1 mg of alum.
[b] Animals were injected intravenously with either saline or 10 μg of protein of anti-T$_{HF}$ daily for three days. On the next day all animals were immunized with ovalbumin.
[c] IgE responses were measured in duplicate by PCA in Sprague-Dawley rats. The mean titers and the range (in parenthesis) of responses are indicated.

Table 8 compares the ability of anti-T$_{HF}$, anti-IgE$_{id}$, and the F(ab)$_2$ fragment of anti-T$_{HF}$ to induce T$_S$ cells. Although anti-IgE$_{id}$ is as effective as anti-T$_{HF}$ in inducing T$_S$ cells, the F(ab)$_2$ fragment of anti-T$_{HF}$ does not significantly induce T$_S$ cells.

TABLE 8

In vivo induction of supressor T cells by anti-idiotypic antibody.

| Immunization[a] | Number of cells transferred | Number of recipients[b] | IgE response[c] 0 100 200 400 600 800 1200 1600 |
|---|---|---|---|
| anti-T$_{HF}$ | $3 \times 10^7$ | 15 | |
| anti-IgE$_{id}$ | $5 \times 10^7$ | 6 | |
| anti-T$_{HF}$(Fab)$_2$[d] | $5 \times 10^7$ | 8 | |
| anti-T$_{HF}$ | $3 \times 10^{7e}$ | 6 | |
| nRGG[f] | $2.5 \times 10^7$ | 12 | |

[a] Animals injected intravenously daily for 3 days with 10 μg anit-T$_{HF}$, 50 μg anti-E$_{id}$, or 80 μg of anti-T$_{HF}$(Fab)$_2$. On day 4 spleens were removed, single cell suspension prepared, and the indicated number of viable cells injected into recipients.
[b] Recipients were primed with 10 μg of WST in alum 20 days earlier, and all animals were given a secondary challenge within 24 hours after receiving cell transfers.
[c] IgE response measured in duplicate in Sprague-Dawley rats. The mean of the maximum responses (day 7) is reported, and the range of responses is indicated by the bars.
[d] Pepsin digest of anti-T$_{HF}$ and passed over a Sepharose-Protein A adsorbent.
[e] Anti-Thy 1.2 and C' treated.
[f] Normal rabbit IgG eluted from Sepharose Protein A adsorbent and injected into donor mice at 10 μg of protein per day for 3 days.

At the concentrations used, both anti-idiotypic antibodies (anti-T$_{HF}$ and anti-IgE$_{id}$) completely suppressed primary anti-AgB IgE responses, and up to 75% of the secondary response in recipients immunized with WST adsorbed on alum (Table 4). The duration of the anti-idiotypic induced suppression was fairly long lived, lasting more than 35 days. The observed suppression is mediated by a T cell population as indicated by abrogation of suppression by treating cells from anti-idiotypic antibody treated animals with anti-thy 1.2 antisera and complement, and the enrichment of the suppressor cell populations in the fraction nonadherent to anti-mouse-Ig-coated petri dishes (Tables 5 and 6). The failure of mice treated with anti-idiotypic antibody prior to immunization with ovalbumin to yield antibody titers different from control mice (treated with saline or nRGG) not only indicates the specificity of anti-idiotype-induced suppressor T cells, but also argues against the suppression being an anti-immunoglobulin-induced feedback mechanism (Table 7).

The failure of the F(ab)$_2$ fragment of anti-T$_{HF}$ antibody to induce a suppressor cell population could reflect a difference in half-life of the intact antibody in the circulation compared to the fragment. It was attempted to overcome this potential problem by using up to eight times (80 μg of protein) the amount of the F(ab)$_2$ fragment compared to the intact (10 μg of protein) anti-idiotypic antibody without success. The F(ab)$_2$ fragment of anti-T$_{HF}$ antibody retained its full combining site activity as demonstrated by its ability to completely block the antigen-induced PCA activity of sera from mice having an AgB-specific IgE titer of 30,000. Others have similarly reported that F(ab)$_2$ fragments of anti-idiotypic antibodies are ineffective immunosuppressants [Rowley, D. A., Fitch, F. W., Stuart, F. P., Kohler, H., and Cosenza, H., Science 181: 1133 (1973); Fitch, F. W. Prog. Allergy 19: 195 (1975); Forni, L., and Pernis, B., Membrane Receptors of Lymphocytes, American Elsevier, N.Y., (1975); Sidman, C. L., and Unanue, E. R., J. Exp. Med. 144: 882 (1976); Pierce, S. K., and Klinman, N. R., J. Exp. Med. 146: 509 (1977); and Moretta, L., Mingari, M. C., and Romanzi, C. A., Nature 272: 618 (1978)]. Recently, several investigators have suggested that B cells may play an important role in the activation of T cell function [Zubler, R. H., Benacerraf, B., and Germain, R. N., J. Exp. Med. 151: 677 (1980); Zubler, R. H., Benacerraf, B., and Germain, R. N., J. Exp. Med. 151: 681 (1980); L'age-Stehr, J., Teichmann, H., Gershon, R. K. and Cantor, H., Eur. J. Immunol. 10: 21 (1980); and Black, S. J. and Herzenberg, L. A., J. Exp. Med., 150: 174 (1979)]. The failure of the F(ab)$_2$ fragment of anti-T$_{HF}$ antibody to induce a suppressor cell population may reflect that either macrophages or B cell processing via their F$_c$ receptors is needed. Alternatively, T cells with F$_c$ receptors [Setcavage, T. M. and Kim, Y. B., J. Immunol. 124: 553 (1980)] may play an important role in the induction of suppressor T cells.

Characterization of the suppressor cell induced by anti-idiotypic antibody indicates that it is a Thy 1+ Lyt 1$^-$23$^+$ T cell. Preliminary studies demonstrated that the factor extracted from spleen cells treated with anti-T$_{HF}$ antibody and nonadherent to anti-mouse-Ig-coated petri dishes binds to idiotype-positive affinity adsorbents (Sepharose-antigen-B-specific suppressor factor) suggesting that the suppressor T cell induced is a T$_{S2}$ suppressor cell population.

EXAMPLE 3

Induction of suppressor T-cells (T$_S$)

CBA/CaxC57BL6 F$_1$ mice and Sprague-Dawley rats were bred under specific pathogen-free conditions at the National Institute for Medical Research (NIMR), Mill Hill, London. In most experiments male mice 9 to 12 weeks old and rats weighing 200 to 250 g were used.

Animals treated with WST were injected intraperitoneally (i.p.) with 10 μg of protein of WST adsorbed on 1 mg of alum on day 0. Animals were given a secondary antigen challenge with the same dose of WST in alum on day 21.

Animals treated with ovalbumin (OVA) were injected i.p. into 10 μg of protein of OVA adsorbed on 1 mg of alum on day 0, and were given a secondary antigen challenge with the same dose of OVA in alum on day 21.

Normal rabbit IgG (nRGG) was prepared by passing normal rabbit serum over a Sepharose-protein A adsorbent, and after washing the adsorbent with seven columns (about 100 ml) of buffer the bound rabbit IgG was eluted with 3 M KSCN in phosphate-buffered saline (PBS), pH 7.2. Gel-diffusion analysis of the isolated fraction gave a single precipitin band against anti-rabbit IgG and anti-whole rabbit sera.

Anti-Lyt 1 and anti-Lyt 2 antisera were obtained from NIMR, Mill Hill, London, and were derived from monoclonal cell lines obtained from Stanford University, Stanford, Calif. Anti-thy 1.2 antisera was obtained from NIMR, Mill Hill, London, and was derived from a monoclonal cell line designated NIMR-1.

Normal spleen cells were removed by aseptic methods, washed three times with sterile RPMI-1640 media, and diluted in complete media to $10^7$ viable cells/ml. Complete media consisted of RPMI-1640 medium supplemented with 25 mM HEPES, 12 mM $NaHCO_3$, sodium pyruvate (1 mM), 2-mercaptoethanol ($2 \times 10^{-5}$ M), 10% fetal calf serum (FCS), L-glutamine (2 mM), nonessential amino acids, and penicillin/streptomycin (100 U and 10 μg/ml). Cultures consisted of $10^7$ normal spleen cells (1 ml of cell suspension) in each mini-Marbrook chamber (Hendley Engineering, Loughton, England) placed in $100 \times 15$ mm sterile Falcon tissue culture dishes containing 10 ml of complete media. The cell suspensions were maintained in the mini-Marbrook chambers by washed and boiled dialysis tubing cut to the appropriate size. All cultures were maintained for 4 days in a moist atmosphere containing 10% $CO_2$, 7% $O_2$, and 83% $N_2$ at 37° C. Upon termination of the cultures, the cells are washed three times, counted, and various numbers of viable cells were injected intravenously into mice primed 20 days earlier with 10 μg of protein of WST adsorbed on 1 mg of alum. All recipients were given a secondary antigen challenge within 24 hours with the same dose of WST in alum.

Serum IgE titers were determined by passive cutaneous anaphylaxis (PCA) in Sprague-Dawley rats. All titrations were done in duplicate, and the mean titers and range of response (in parenthesis) are reported.

Serum IgG titers were analyzed by a radioimmunoassay using WST-conjugated paper disks and the level of timothy-specific IgG antibodies was less than 100 ng of IgG.

An indirect microtiter plate ELISA to measure AgB-specific $T_{SF1}$ and $T_{SF2}$ was developed according to the method of Voller et al [Manual of Clin. Imm. Ed. by N. Rose et al, Pg. 506 (1976) Amer. Soc. Microbiol.] with some modification. Rabbit anti-$T_{HF}$ and sheep anti-rabbit IgG antibodies were prepared as above. Sheep anti-rabbit IgG (0.8 mg) in 0.5 ml was dialyzed extensively with PBS, pH 7.2, at 4° C. with alkaline phosphatase (Miles Laboratories, Inc., Elkhart, Ind.) and conjugated with 0.2% gluteraldehyde. Excess gluteraldehyde was removed by additional dialysis against PBS, pH 7.2, at 4° C., and the final conjugate was mixed human serum albumin (3% final concentration), and sodium azide (0.02% final concentration). Flat-bottomed micro ELISA polystyrene plates (Dynatech Laboratories, Inc., Alexandria, Va.) were coated with 200 μl of affinity purified AgB-specific T helper factor ($T_{HF}$) containing 475 μg of protein/ml by incubation at 37° C. for 3 hours. The plates were washed with a PBS-Tween-20 buffer and incubated overnight at 4° C. with 50 μg (150 μl) of affinity purified anti-$T_{HF}$. The plates were washed with PBS-Tween-20, and incubated for 3 hours at 37° C. with sheep anti-rabbit IgG enzyme conjugate (1/25 dilution). The plates were washed with PBS-Tween-20, then substrate buffer, and finally incubated at 37° C. for 90 min. with p-nitrophenyl phosphate (Sigma 104, St. Louis, Mo.) (1 mg/ml). The reaction was stopped by the addition of 50 μl of 3 M NaOH and the developed color was measured spectrophotometrically at 405 nm.

Antigen B-specific $T_{SF}$ was quantitated by inhibition of anti-$T_{HF}$ binding to microtiter plate bound $T_{HF}$. Anti-$T_{HF}$ (50 μg of protein) is incubated with varying concentrations of $T_{SF}$ for 2 hours at room temperature before adding this mixture to the $T_{HF}$-coated microtiter plates and incubated overnight at 4° C. The soluble factor extracted from $T_{S2}$ cells, anti-idiotype factor ($T_{SF2}$) is determined by addition of affinity purified material (Sepharose-$T_{SF}$) to $T_{HF}$ bound microtiter plates for 2 hours at room temperature prior to the addition of anti-$T_{HF}$ and incubation overnight at 4° C.

Cultures of normal spleen cells with anti-idiotypic antibody (anti-$T_{HF}$ and anti-IgE$_{id}$) yield a population of $T_S$ cells that significantly suppress a secondary IgE response in recipients (Table 9). Animals similarly treated with cells cultured with $\overline{n}$RGG have the same secondary IgE response as animals given only a primary and secondary antigen challenge. The suppression induced by spleen cells cultured with anti-idiotypic antibody (anti-Id) is lost upon treatment of these cells with anti-thy 1 antisera and guinea pig complement (C) suggesting that the observed suppression is due to suppressor T cells. Anti-Id between the concentrations of 10 to 100 μg appears to be equally effective in inducing a population of suppressor T ($T_S$) cells (Table 9).

TABLE 9

| | | | | | | |
|---|---|---|---|---|---|---|
| Anti-idiotypic antibody induction of suppressor T cells in vitro. | | | | | | |
| | | | No. of | IgE response[c] | | |
| | Dose | No. of cells | recipi- | Day | | |
| Treatment[a] | (μg) | transferred[b] | ents | 7 | 10 | 14 |
| anti-$T_{HF}$ | 10 | $4 \times 10^6$ | 6 | 50(0–100) | 0 | 0 |
| | 25 | $6 \times 10^6$ | · 9 | 50(0–100) | 0 | 0 |
| | 50 | $8 \times 10^6$ | 15 | 200(50–400) | 50 | 0 |
| | 100 | $8 \times 10^6$ | 15 | 100(0–200) | 0 | 0 |
| | 100 | $5 \times 10^{6d}$ | 6 | 1600 | 800 | 200 |
| anti-IgE$_{id}$ | 50 | $3.5 \times 10^6$ | 4 | 100(0–200) | — | 0 |
| nRGG | 100 | $5 \times 10^6$ | 12 | 1600 | — | 400 |
| | | | | | | (200) |

TABLE 9-continued

Anti-idiotypic antibody induction of suppressor T cells in vitro.

| Treatment[a] | Dose (μg) | No. of cells transferred[b] | No. of recipients | IgE response[c] Day 7 | 10 | 14 |
|---|---|---|---|---|---|---|
| none | — | — | 15 | 1600 | — | 400 |

[a]Normal spleen cells ($10^7$) were cultured in mini-Marbrook chambers with anti-$T_{HF}$, anti-IgE$_{id}$, or nRGG for 4 days at 37° in 10% $CO_2$ and 7% $O_2$.
[b]Upon completion of culture, cells are washed three times in PBS, pH 7.2, counted, and the indicated number of viable cells were injected intravenously into recipients primed 20 days earlier with 10 μg of WST adsorbed on 1 mg of alum. Recipients were given a secondary antigen challenge with the same dose of WST within 24 hours after cell transfer.
[c]IgE measured by PCA in Sprague-Dawley rats in duplicate. Mean response is reported and the range of response where observed is indicated by parenthesis.
[d]Cells cultured with 100 μg of anti-$TH_F$ and treated with anti-thy 1 sera and complement prior to the cells being injected intravenously into recipients.

Previous studies comparing the effectiveness of intact anti-$T_{HF}$ and the F(ab)$_2$ fragment of anti-$T_{HF}$ antibody to induce $T_S$ cells in vivo showed that the F(ab)$_2$ fragment of anti-$T_{HF}$ was unable to induce $T_S$ cells. Since the in vivo persistance of the intact and F(ab)$_2$ fragment of anti-$T_{HF}$ differs significantly, the ability of the F(ab)$_2$ fragment to induce $T_S$ cells in the in vitro culture system was reevaluated. Table 10 shows that the F(ab)$_2$ fragment of anti-$T_{HF}$ cultured 4 days with normal spleen cells fails to induce $T_S$ cells. In addition, cultures of B-cell-depleted (cells nonadherent to anti-mouse IgM-coated petri dishes) spleen cells with anti-$T_{HF}$ antibody did not result in the induction of $T_S$ cells (Table 10).

TABLE 10

The requirement of $F_C^+$ cells for the in vitro induction of suppressor T cells by anti-idiotypic antibody.

| Treatment[a] | Dose (μg) | Source of normal cells | No. of cells transferred[b] | No. of recipients | IgE response[c] Day 7 | 14 |
|---|---|---|---|---|---|---|
| nRGG | 100 | spleen | $5 \times 10^6$ | 4 | 1600 | 600 |
| anti-$T_{HF}$ | 50 | spleen | $5 \times 10^6$ | 8 | 50 | 0 |
| anti-$T_{HF}$ F(ab)$_2$d | 60 | spleen | $7 \times 10^6$ | 4 | 1600 | 400 |
| anti-$T_{HF}$ | 50 | B cell depleted[e] | $7 \times 10^6$ | 6 | 1250 | 600 |

[a]Normal spleen cells ($10^7$) were cultured in mini-Marbrook chambers with the indicated doses of nRGG, anti-$T_{HF}$, or the F(ab)$_2$ fragment of anti-$T_{HF}$ for 4 days at 37° in 10% $CO_2$ and 7% $O_2$.
[b]Upon completion of culture, cells were washed three times in PBS, pH 7.2, counted, and the indicated number of viable cells were injected intravenously into recipients primed 20 days earlier with 10 μg of WST adsorbed on 1 mg of alum. Recipients were given a secondary antigen challenge with the same dose of WST within 24 hours after cell transfer.
[c]IgE measured by PCA in Sprague-Dawley rats in duplicate and the mean response is reported.
[d]Pepsin digest of anti-$T_{HF}$ antibody isolated by passage over a Sepharose-protein A adsorbent.
[e]Spleen cells nonadherent to sheep anti-mouse IgM coated petri dishes.

In an effort to determine the nature of $T_S$ cells induced by anti-Id, normal spleen cells were cultured with 100 μg of anti-$T_{HF}$ antibody, or 100 μg of nRGG. Upon determination of the cultures, the cells were washed three times with PBS, pH 7.2, and the cells frozen (at $-20°$ C.) and thawed (at $37°$ C.) three times. The cell-free supernatant from pooled lysates was obtained by centrifugation at 20,000 rpm in a Beckman ultracentrifuge, and stored at $-20°$ C. until passed over Sepharaose-AgD and Sepharose-$T_{SF}$ adsorbents. Table 11 shows that both $T_{SF1}$ and $T_{SF2}$ factor were extracted from spleen cells cultured with anti-Id. On the other hand, neither $T_{SF1}$ nor $T_{SF2}$ was extracted from spleen cells cultured with nRGG. The level of $T_{SF1}$ and $T_{SF2}$ factor present in each cell-free supernatant was determined by an ELISA of material eluted from Sepharose-AgD and Sepharose-$T_{SF}$ adsorbents.

TABLE 11

Soluble factors extracted from normal spleen cells cultured with anti-$T_{HF}$ antibody.

| Cells cultured with | Dose (μg) | Factors eluted from Sepharose-AgD $T_{SF2}/10^8$ cells | Sepharose-$T_{SF}$ ald/$10^8$ cells |
|---|---|---|---|
| anti-$T_{HF}$ | 100 | 0.44 mg | 0.14 mg |
| nRGG | 100 | 0 | 0 |

EXAMPLE 4

In vitro induction of suppressor T cells with antigen B-specific T suppressor factor

TABLE 12

| Treatment[a] | Dose (μg) | No. of cells transferred[b] | No. of recipients | IgE response[c] Day 7 | 14 |
|---|---|---|---|---|---|
| nRGG | 50 | $8 \times 10^6$ | 4 | 1600 | 600 |
| $T_{SF}$[d] | 5 | $5 \times 10^6$ | 6 | 1000 | 400 |
| | 25 | $5 \times 10^6$ | 8 | 700 | 100 |
| | 50 | $5 \times 10^6$ | 6 | 100 | 0 |
| | 100 | $5 \times 10^6$ | 4 | 100 | 0 |
| | 100 | $7 \times 10^6$[e] | 4 | 1600 | 400 |
| $T_{SF2}$[f] | 50 | $5 \times 10^6$ | 4 | 0 | 0 |

[a]Normal spleen cells ($10^7$) were cultured in mini-Marbrook chambers with nRGG or $T_{SF}$ for 4 days at 37° in 10% $CO_2$ and 7% $O_2$.
[b]Upon completion of culture, cells are washed three times in FBS, pH 7.2, counted, and the indicated number of viable cells were injected intravenously into recipients primed 20 days earlier with 10 g of WST adsorbed on 1 mg of alum. Recipients were given a secondary antigen challenge with the same dose of WST within 24 hours after cell transfer.
[c]IgE measured by PCA in Sprague-Dawley rats in duplicate and the mean response is reported.
[d]Represents antigen B-specific T suppressor factor ($T_{SF}$) isolated by affinity chromatography on Sepharose-antigen D.
[e]Cells cultured with 100 μg of $T_{SF}$ and treated with anti-thy 1 sera and complement prior to the cells being injected intravenously into recipients.
[f]Antigen B specific T-suppressor factor ($T_{SF2}$) isolated by affinity chromography on Sepharose-$T_{SF}$.

EXAMPLE 5

Induction of $T_S$ cells with Ox-AgB and preparation of $T_{SF}$.

Timothy pollen extract (WST), purified AgB, Ox-AgB, antigen D$_1$ (AgD$_1$), and keyhole limpet (Megathura crenulata) hemocyanin (KLH) were prepared as described [Malley, A., Baecher, L., Begley, D., Dev. Biol. Standard, 29: 29 (1975); Malley, A., Begley, D., and Forsham, A., Immunochemistry (in press, 1979); Campbell, D. H., Garvey, J. S., Cremer, N. E., Sussdorf, D. H., Methods in Immunology, p. 69 (Benjamin, New York, 1963)]. The protein content of the samples was determined by the method of Lowry [Markwell, M. A. K., Haas, S. M., Beiber, L. L., and Tolbert, N. E., Analyt. Biochem. 87: 206 (1978)]. The carbohydrate content of the suppressor factor was described by the orcinol method [Ashwell, G., Methods in Enzymology, VIII: 94 (1966)].

LAF$_1$ mice (Jackson Laboratory, Bar Harbor, Me.) were immunized with 10 μg of WST adsorbed to 1 mg of alum on days 0 and 21; 7 days later spleen cells were removed to obtain immune spleen cells.

LAF$_1$ mice received 100–200 μg of Ox-AgB in complete Freund's adjuvant (CFA) in each of two injections at a 14-day interval. Seven days after the second priming, spleen cells were removed; these either were used in adoptive transfer to measure $T_S$ cells or were placed in culture with isolubilized antigen (Sepharose-AgD$_1$) to obtain secreted T$_S$ factor (T$_{SF}$)

For the kinetics studies, animals received 200 μg of Ox-AgB in CFA in each of two injections at a 14-day interval. Spleen cells were removed 3, 7, 10, 14 and 21 days after the second treatment with Ox-AgB. Immunizations were scheduled so that spleen cell removal for all groups fell on a single day.

Immune spleen cells were obtained from mice immunized with 10 μg of protein of WST. A single-cell suspension was prepared as described by Fairchild, S. S.; Malley, A., J. Immun. 97: 559 (1966), and 1.5–2×10$^8$ cells were applied to nylon wool columns to provide immune T cells [Julius, M. H.; Simpson, E., and Herzenberg, L. A., Eur. J. Immunol. 3: 645 (1973)]. Immune B cells were prepared by treatment of immune spleen cells (10$^7$ cells/ml) with rabbit anti-thy 1.2 sera (Accurate Chemical Co., Hicksville, N.W.) and guinea pig complement (Colorado Serum Co., Denver, Colo.), at a final dilution of 1:10.

Syngeneic X-irradiated (600 rad) mice received i.v. injections of 2.5×10$^4$ immune B cells and 4×10$^4$ immune T cells. Within 4 hours all animals were challenged i.p. with 10 μg of WST in alum; blood samples were collected 7, 10, and 14 days later. The maximum IgE response was obtained 7 days after antigen challenge and reached an IgE titer of 800.

When suppressor cells were tested, 5×10$^7$ cells from mice immunized with Ox-AgB in CFA or 5×10$^7$ normal spleen cells were added and injected i.v. with the immune T and B cells. When suppressor factor was being assayed, a cell-free supernatant (CFS) equivalent to 5×10$^7$ cells was added to the mixture of immune T and B cells and was injected i.v. into syngeneic X-irradiated recipients. The IgE titers (reciprocal of the lowest dilution giving a positive reaction) were measured by passive cutaneous anaphylaxis (PCA) as described by Ovary et al, J. Immun. 97: 559 (1966); and Fairchild et al, J. Immun. 115: 446 (1975); IgG responses were evaluated by a modified version of the radioallergosorbent test [Malley et al, Int. Archs. Allergy Appl. Immun. 62: 276 (1980)] with AgB-conjugated Whatman 3-mm paper disks.

The Sepharose-AgD$_1$, adsorbent was prepared in the following manner. Sepharose-AH-4B (Pharmacia Fine Chemicals, Piscataway, N.J.) was washed with 0.5 M NaCl, water, and 1.0 M NaH-CO$_3$, pH 9. 50 mg of AgD$_1$ were added to 10 ml of 0.5 M NaHCO$_3$ (pH 9), and the pH of the AgD$_1$ solution was adjusted to pH 10.5 just prior to addition of cyanogen bromide in dimethylformamide. 1.5 g of CNBr dissolved in 2 ml of dimethylformamide were added dropwise to the magnetically stirred AgD$_1$ solution; the pH was maintained between 10.0 and 10.7 by the addition of 5 N NaOH. When the pH was stable (within 10–15 min.), this solution was added to the Sepharose-AH slurry. Additional (10 ml) 0.1 M NaHCO$_3$ buffer (pH 9) was used to wash out the vessel, and the wash was added to the mixture and stirred at 4° C. overnight (20 hours).

The AgD$_1$-conjugated Sepharose-AH was then filtered on a coarse sintered glass filter, and the matrix was washed with 300 ml of 0.1 M NaHCO$_3$ buffer, pH 9. The Sepharose-AH-AgD$_1$ was transferred to a beaker and stirred for 3 hours at room temperature with 1.0 M ethanolamine in 0.1 M NaHCO$_3$, pH 9. The matrix was washed on a sintered glass filter with the following solutions (250 ml each): 0.1 M NaHCO$_3$-0.5 M NaCl, pH 10; distilled water; 0.1 M NaAc-0.5 M NaCl, pH 4; distilled water; 2 M urea-0.5 M NaCl; distilled water; and 0.01 M cacodylate buffer-0.155 M NaCl, pH 7.0. The Sepharose-AgD$_1$ adsorbent was stored at 4° C. in 0.01 M cacodylate-saline buffer (CSB), pH 7.0.

Spleen cells from mice immunized with Ox-AgB in CFA were used to obtain secreted soluble T$_{SF}$. Each culture contained 1 ml of cells (5×10$^4$ cells/ml) in RPMI 1640 supplemented with 5% heat-inactivated fetal calf serum. Antigenic stimulation of these primed cells was achieved by addition of one of the following: 100 μg of soluble AgB; 100 μg of a 1:5 suspension of Sepharose-AgB; or 100 μl of a 1:5 suspension of a Sepharose-AgD$_1$ conjugate in RPMI 1640. Cultures were incubated at 37° C. for 24, 48, or 72 hours in 5% CO$_2$ and 95% air. Upon completion of these cultures, the cells were centrifuged and the CFSs were collected. Each CFS was tested by adoptive transfer for the presence of T$_{SF}$. Recipients were given CFS equivalent to 5×10$^7$ cells and immune T and B cells. Blood samples were obtained 7 and 14 days later, and IgE antibody titers were determined by PCA.

Immune spleen cells from mice primed twice with 100 μg of Ox-AgB in CFA (as described above) were sonicated in a Biosonik III apparatus (Bronwill Sci., Rochester, N.Y.) at 42 W/cm$^2$. The cells in 2 ml of media were placed in a 12×100 mm centrifuge tube and sonicated for 1.5 min. in an ice bath. The sonicate was centrifuged at 20,000 rpm for 30 min. at 4° C., and the CFS was collected and assayed for suppressor factors.

Spleen cells from mice primed with Ox-AgB in CFA were used to prepare both sonicate-derived and secreted soluble suppressor factors. Sonicate-derived (T$_{SF-E}$) or secreted T suppressor factor (T$_{SF-S}$) was passed over a Sepharose-AgD$_1$ adsorbent (10 ml of packed resin) equilibrated in CSB, pH 7. The nonadherent protein fraction was washed through the adsorbent with CSB, and the adsorbent was washed with 5–10 column volumes. The adherent fraction was eluted with 15 ml of 3 M KSCN in CSB, and the adsorbent was washed with an additional 100 ml of CSB. The first 35–50 ml of eluted material was collected, dialyzed, concentrated by negative pressure against CSB. Both nonadherent and adherent fractions were tested for the presence of suppressor factor by adoptive transfer.

The suppresive capacity of spleen cells from mice primed with Ox-AgB in CFA is shown in Table 12. In previous studies [Malley et al, Int. Archs. Allergy Appl. Immun. 62:276 (1980)], adoptive transfer recipients receiving 4×10$^6$ WST-immune T cells and 2.5×10$^6$ WST-immune B cells and challenged with 10 μg of WST in alum produced a maximum IgE response (PCA titer of 800) 7 days later. The addition of 5×10$^7$ spleen cells from mice primed with CFA only to this mixture of WST-immune T and B cells did not reduce the secondary IgE response obtained in adoptive transfer recipients. In contrast, spleen cells from mice primed with Ox-AgB in CFA added to the mixture of immune cells resulted in dose-dependent suppression of the secondary IgE response. Treatment of the Ox-AgB-primed spleen cells with anti-thy 1.2 sera and guinea pig complement resulted in a complete loss of suppressive activity in the remaining cells. Antigenic specificity of the T$_S$ cells for AgB was demonstrated by the failure of Ox-AgB-primed spleen cells to influence a secondary IgE response to ovalbumin in synageneic X-irradiated recipients.

TABLE 12

Suppression of the anti-antigen-B IgE response by T suppressor cells

| Source of cells | Number of cells | Ratio immune cells[1] T:B | Irradiated recipients[2] | PCA titer[3] |
|---|---|---|---|---|
| Ox—AgB CFA[4] | $5 \times 10^7$ | 1.6:1 | 10 | 0 |
| Ox—AgB CFA | $2.5 \times 10^7$ | 1.6:1 | 10 | 200 |
| Ox—AgB CFA | $10^7$ | 1.6:1 | 10 | 400 |
| Ox—AgB CFA | $5 \times 10^6$ | 1.6:1 | 10 | 800 |
| Ox—AgB CFA[5] | $5 \times 10^7$ | 1.6:1 | 3 | 800 |
| FCA only[6] | $5 \times 10^7$ | 1.6:1 | 3 | 800 |

[1]Mice were primed twice with 10 μg of WST adsorbed on 1 mg of alum at 21-day intervals. Spleen cells were prepared 7 days later. Immune T cells represent nylon wool-nonadherent cells ($1.5 \times 10^8$ cells applied to column); immune B cells represent spleen cells treated with anti-thy 1.2(1:10) and guinea pig complement (1:10).
[2]All cells were injected i.v. into X-irradiated (600 rad) syngeneic mice, and were challenged with 10 μg of WST adsorbed on 1 mg of alum within 4 hours after injection of the cells.
[3]Passive cutaneous anaphylaxis was accomplished in duplicate; the indicated titer represents the reciprocal of the lowest dilution with a 5 × 5 mm reaction.
[4]Mice were primed twice with 100 μg of Ox—AgB in CFA at 14-day intervals, and the spleen cells were prepared 7 days later.
[5]Spleen cells from mice primed with Ox—AgB in CFA and treated with anti-thy 1.2 sera and guinea pig complement.
[6]Spleen cells from mice primed with CFA only.

The kinetics of $T_S$ cell induction in mice primed with Ox-AgB in CFA at 14-day intervals is shown in Table 13. Although some $T_S$ cells were evident within 3 three days after the last injection of Ox-AgB, the maximum level of induction occurred between days 7 and 14 and $T_S$ cells were absent in the spleen 21 days after Ox-AgB injection. In subsequent studies designed to either evaluate the activity of such cells or isolate $T_{SF}$, spleen cells from Ox-AgB-primed mice were obtained 7–10 days after the last injection of Ox-AgB.

TABLE 13

Kinetics of the induction of T suppressor cells with antigen B modified by photooxidation.

| Days after last injection of Ox—AgB[1] | Ratio of cells used in adoptive transfer[2] | Number of recipients | PCA titer[3] |
|---|---|---|---|
| 3 | 1.6:1 | 6 | 200 |
| 7 | 1.6:1 | 6 | 50 |
| 10 | 1.6:1 | 6 | 100 |
| 14 | 1.6:1 | 6 | 0 |
| 21 | 1.6:1 | 6 | 800 |
| None[4] | 1.6:1 | 6 | 800 |

[1]Mice were primed twice with 200 μg of Ox—AgB in CFA at 14-day intervals; spleen cells were collected at the indicated interval after the last injection of Ox—AgB.
[2]Mice were primed with 10 μg of WST adsorbed on 1 mg of alum at 21-day intervals. Spleen cells were prepared 7 days later. Immune T cells represent nylon wool nonadherent cells; immune B cells represent spleen cells treated with anti-thy 1.2 (1:10) and guinea pig complement (1:10). Immune T and B cells were mixed in a ratio of 1.6:1 ($4 \times 10^6$ T/$2.5 \times 10^6$ B cells) with $5 \times 10^7$ Ox—AgB-primed cells and injected i.v. into X-irradiated (600 rad) syngeneic mice. All recipients were challenged with 10 μg of WST adsorbed on 1 mg of alum within 4 hours after injection of the cells.
[3]Passive cutaneous anaphylaxis was accomplished in duplicate in Sprague-Dawley rats. The indicated titer represents the reciprocal of the lowest dilution with a 5 × 5 mm reaction.
[4]Spleen cells from mice primed with CFA only (cells were collected 7 days later).

The conditions for the secretion of $T_{SF-S}$ (S-secreted) from Ox-AgB-specific cells are shown in Table 14.

TABLE 14

Tissue culture conditions for the secretion of soluble T suppressor factor.

| Source of cells | Culture conditions[1] antigen | time, h | Ratio of cells used in adoptive transfer[2] | Number of recipients | PCA titer[3] |
|---|---|---|---|---|---|
| Ox—AgB/CFA | sonicated[4] | — | 1.6:1 | 6 | 200 |
| Ox—AgB/CFA | AgB | 24 | 1.6:1 | 6 | 800 |
|  | Sepharose-Ox—AgB | 24 | 1.6:1 | 6 | 800 |
|  | Sepharose-AgD$_1$ | 24 | 1.6:1 | 6 | 800 |
| Ox—AgB/CFA | AgB | 72 | 1.6:1 | 6 | 800 |
|  | Sepharose-Ox—AgB | 72 | 1.6:1 | 6 | 100 |
|  | Sepharose-AgD$_1$ | 72 | 1.6:1 | 6 | 100 |
| KLH/CFA[5] | Sepharose-Ox—AgB | 72 | 1.6:1 | 6 | 800 |
|  | Sepharose-AgD$_1$ | 72 | 1.6:1 | 6 | 800 |

[1]Upon completion of tissue culture, the cells were removed by centrifugation and the cell-free supernatant (CFS) collected. The amount of CFS mixed with immune T and B cells was based upon the number of cells used to obtain the CFS ($5 \times 10^7$ cell equivalents).
[2]Mice were primed with 10 μg of WST adsorbed on 1 mg of alum at 21-day intervals and spleen cells were prepared 7 days later. Immune T cells represent nylon wool nonadherent cells; immune B cells represent spleen cells treated with anti-thy1.2 sera (1:10) and guinea pig complement (1:10). Immune T and B cells ($4 \times 10^6$ T, $2.5 \times 10^6$ B) were mixed with $5 \times 10^7$ cell equivalents obtained from Ox—AgB-primed cells either sonicated or cultured for 24–72 hours with antigen. These mixtures were injected i.v. into X-irradiated (600 rad) syngeneic recipients, and they were challenged with antigen within 4 hours.
[3]Passive cutaneous anaphylaxis was accomplished in duplicate; the indicated titer represents the reciprocal of the lowest dilution with a 5 × 5 mm reaction.
[4]Cells primed with 100 g of Ox—AgB in CFA were sonicated at 42 W/cm$^2$ in a 12 × 100 mm tube for 1.5 min. on ice and centrifuged at 20,000 rpm for 30 min. at 4° C. The sonicate was collected and assayed for extracted suppressor factor.
[5]Spleen cells from mice primed with KLH in CFA were cultured for 72 hours with insolubilized antigen (Ox—AgB and AgD$_1$) and the CFS collected.

Extraction of $T_{SF-E}$ (E-extracted) by sonication of $T_S$ cells results in the recovery of suppressor factor. The CFS (equivalent to $5 \times 10^7$ cells) containing $T_{SF-E}$ resulted in a 75% suppression of the AgB-specific IgE response. Attempts to induce the secretion of $T_{SF-S}$ from Ox-AgB-specific $T_S$ cells with soluble AgB or insolubilized Ox-AgB or AgD$_1$ during a 24-hour culture period were unsuccessful. However, Ox-AgB-specific $T_S$ cells cultured for 72 hours with insolubilized antigen (Ox-AgB or AgD$_1$) secreted a significant amount (88% suppression) of $T_{SF-S}$ into the culture supernatant. This factor was not secreted from Ox-AgB-primed $T_S$ cells cultured with soluble antigen for 72 hours.

Partial purification of $T_{SF}$ was achieved by affinity chromatography on a Sepharose-AH-Ox-AgB or Sepharose-AH-AgD$_1$ adsorbent equilibrated in 0.01 M CSB, pH 7. Material not adhering to the Sepharose-AgD$_1$ adsorbent did not contain any T$_{SF}$ activity, but material eluted from the adsorbent with 3 M KSCN contained significant levels of this activity (Table 15). Analysis of T$_{SF-E}$ and T$_{SF-S}$ for protein and carbohydrate composition indicated that both partially purified factors contained about 5% carbohydrate and 95% protein.

TABLE 15

Partial purification of antigen B-specific T suppressor factor by affinity chromatography.

| Source spleen cells | Treatment | Cell equivalents[1] | Ratio of cells used in adoptive transfer[2] | Number of recipients | PCA titer[3] |
|---|---|---|---|---|---|
| CFA only | sonicate | 5 × 10$^7$ | 1.6:1 | 6 | 800 |
| Ox—AgB/CFA | sonicate | 5 × 10$^7$ | 1.6:1 | 6 | 100 |
| Ox—AgB/CFA | sonicate[4] Sepharose-AgD$_1$ nonadherent | 5 × 10$^7$ | 1.6:1 | 6 | 800 |
| Ox—AgB/CFA | sonicate[5] Sepharose-AgD$_1$ adherent | 1 × 10$^7$ | 1.6:1 | 6 | 50 |
| Ox—AgB/CFA | CFS(secreted)[6] | 5 × 10$^7$ | 1.6:1 | 6 | 100 |
| Ox—AgB/CFA | CFS(secreted)[7] Sepharose AgD$_1$ nonadherent | 5 × 10$^7$ | 1.6:1 | 6 | 800 |
| Ox—AgB/CFA | CFS(secreted)[8] Sepharose AgD$_1$ bound | 2.5 × 10$^6$ | 1.6:1 | 6 | 0 |

[1]Cell equivalents represent the CFS obtained from a given number of spleen cells treated by sonication or after tissue culture for 72 hours (secreted).
[2]Mice were primed with 10 μg of WST adsorbed on 1 mg of alum at 21-day intervals and spleen cells were prepared 7 days later. Immune T cells represent nylon wool nonadherent cells; immune B cells represent spleen cells treated with anti-thy1.2 sera (1:10) and guinea pig complement (1:10). Immune T and B cells (4 × 10$^6$ T/s, 5 × 10$^6$ B) were mixed with the indicated amounts of material derived from Ox—AgB-primed spleen cells. These mixtures were injected i.v. into X-irradiated (600 rad) syngeneic recipients, and they were challenged with antigen within 4 hours.
[3]Passive cutaneous anaphylaxis was accomplished in duplicate in Sprague-Dawley rats. The indicated titer represents the reciprocal of the lowest dilution with a 5 × 5 mm reaction.
[4]Sonicate is from spleen cells of mice immunized with Ox—AgB/CFA which has been partially purified on a Sepharose-AH—AgB$_1$ adsorbent. Nonadherent fraction was used.
[5]Sonicate is from spleen cells of mice immunized with Ox—AgB/CFA which has been partially purified on a Sepharose-AH—AgD$_1$ adsorbent. Adherent fraction, eluted with 3 M KSCN, was used.
[6]CFS was obtained from spleen cells of mice primed with Ox—AgB in CFA and cultured for 72 hours with insolubilized antigen.
[7]CFS was obtained as in '6' and partially purified on a Sepharose-AH—AgD$_1$ adsorbent. Nonadherent fraction was used.
[8]CFS was obtained as in '6' and partially purified on a Sepharose-AH—AgD$_1$ adsorbent. Adherent fraction, eluted with 3 M KSCN, was used.

I claim:

1. A method of preparing an anti-idiotypic antibody directed against (1) Timothy grass antigen B- and (2) cross reactive grass antigen-specific allergic antibody, IgE, said anti-idiotypic antibody, anti-IgE$_{id}$, being specifically reactive with the idiotypic determinants on said IgE and (1) antigen B- and (2) cross reactive grass antigen-specific T and B cells comprising:
   (1) immunizing a first animal species with a source of antigen B,
   (2) collecting sera from said immunized first animal species,
   (3) separating IgE from said sera,
   (4) immunizing a second animal species with said IgE,
   (5) collecting sera from said immunized second animal species, and
   (6) separating said anti-IgE$_{id}$ antibody from said sera.

2. The method of claim 1 wherein said second animal species is different from said first animal species.

3. The method of claim 1 wherein said first animal species is mouse and said second animal species is rabbit.

4. The method of claim 1 wherein said step (1) includes the step of hyperimmunizing said first animal species with a source of antigen B prior to the collection 5. The antibody anti-IgE$_{id}$.

6. A method of preparing an anti-idiotypic antibody directed against (1) Timothy grass antigen B- and (2) cross reactive grass antigen-specific allergenic T-helper factor, T$_{HF}$, said anti-idiotypic antibody, anti-T$_{HF}$, being specifically reactive with the idiotypic determinants on said T$_{HF}$ and (1) antigen B- and (2) cross reactive grass antigen-specific T and B cells comprising:
   (1) immunizing a first animal species with photooxidized antigen B,
   (2) collecting T$_H$- cells from said immunized first animal species,
   (3) culturing said T$_H$-cells with a source of Timothy grass antigen B or cross reactive grass antigen,
   (4) separating T-helper factor, T$_{HF}$, from said culture,
   (5) immunizing a second animal species with said T-helper factor, T$_{HF}$,
   (6) collecting sera from said immunized second animal species, and
   (7) separating said anti-T$_{HF}$ antibody therefrom.

7. The method of claim 6 wherein said second animal species is different from said first animal species.

8. The method of claim 6 wherein said first animal species is mouse and said second animal species is rabbit.

9. The method of claim 6 wherein said T$_H$-cells are collected from the spleen of said first animal species.

10. The method of claim 6 wherein said first animal species is immunized with photooxidized antigen B adsorbed on alum.

11. The method of claim 6 wherein said culture medium containing T$_{HF}$ is centrifuged and T$_{HF}$ isolated from the cell-free supernatant by affinity chromatography.

12. The method of claim 6 wherein said anti-$T_{HF}$ is isolated from sera by affinity chromatography.

13. The antibody, anti-$T_{HF}$.

14. A method of producing (1) Timothy grass antigen B- and (2) cross reactive grass antigen-specific T suppressor cells, $T_S$, comprising:
   (1) culturing the antibody of claim 5 or 13 with normal cells of an animal to induce the formation of $T_S$ cells in said culture and
   (2) separating said $T_S$ from said culture.

15. The method of claim 14 wherein said normal cells comprise spleen cells.

16. The method of claim 14 wherein said normal cells comprise human peripheral blood lymphocytes.

17. A method of producing Timothy grass antigen B- and crossreactive grass antigen-specific T suppressor cells, $T_S$, comprising:
   1. immunizing an animal species with anti-$IgE_{id}$ and,
   2. collecting $T_s$ cells from said animal species.

18. The method of claim 17 wherein said $T_{S^-}$ cells are derived from the spleen of said immunized animal species.

19. A method of producing (1) Timothy grass antigen B- and (2) cross reactive grass-antigen specific suppressor T-cell factor, $T_{SF}$, by repeatedly freezing and thawing Ts cells and separating said Ts cells from $T_{SF}$.

20. The method of claim 19 wherein said $T_{SF}$ is isolated by affinity chromatography.

21. A method for producing (1) Timothy grass antigen B- and (2) cross reactive grass antigen-specific suppression T-cell factor, $T_{SF}$, comprising:
   (1) culturing T suppressor cells, $T_S$, with antigen-$IgE_{id}$, and
   (2) separating $T_{SF}$ from said cell containing culture.

22. The method of claim 21 wherein said $T_{SF}$ containing medium is centrifuged to obtain a cell-free supernatant and $T_{SF}$ is recovered from said supernatant by affinity chromatography.

23. A method of fractionating $T_{SF}$ into separate factors, $T_{SF1}$ and $T_{SF2}$, comprising the steps of: (1) subjecting $T_{SF}$ to affinity chromatography on an adsorbent comprising Timothy grass antigen $D_1$ on an inert carrier substrate; (2) collecting the non-adsorbing fraction; (3) eluting $T_{SF1}$ adsorbed on said adsorbent and separating $T_{SF1}$ from the eluant; (4) subjecting the non-adherent fraction to affinity chromotagraphy on an adsorbent comprising $T_{SF1}$ on an inert carrier substrate, eluting the $T_{SF2}$ therefrom and separating $T_{SF2}$ from the eluant.

24. The protein fraction $T_{SF2}$.

25. A method of producing Timothy grass antigen B-and cross reactive grass antigen-specific T suppressor cells, $T_S$, comprising:
   (1) culturing $T_{SF1}$ or $T_{SF2}$ with normal cells of an animal species, and
   (2) separating $T_S$ from said normal cell containing culture.

26. A pharmaceutical composition in unit dosage form for suppressing the allergic response of an animal sensitive to Timothy grass antigen B or a cross reactive grass antigen comprising an anti-allergic response effective amount of the product of claims 5, 13, or 24 and a pharmaceutically acceptable carrier therefor.

27. A method for suppressing the allergic response of an animal sensitive to Timothy grass antigen B or a cross reactive grass antigen comprising administering thereto an anti-allergic response effective amount of the product of claims 5, 13, or 24.

28. A pharmaceutical composition in unit dosage form for suppressing the allergic response of an animal sensitive to Timothy grass antigen B or a cross reactive grass antigen comprising an anti-allergic response effective amount of the product when made by the process of claims 19 or 23.

29. A method for suppressing the allergic response of an animal sensitive to Timothy grass antigen B or a cross reactive grass antigen comprising administering thereto an anti-allergic response effective amount of the product when made by the process of claims 19 or 23.

* * * * *